US00PP20394P3

(12) United States Plant Patent
Ackerman et al.

(10) Patent No.: US PP20,394 P3
(45) Date of Patent: Oct. 6, 2009

(54) STRAWBERRY PLANT NAMED 'VALOR'

(50) Latin Name: *Fragaria ananassa*
Varietal Denomination: VALOR

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 12/070,943

(22) Filed: Feb. 21, 2008

(65) Prior Publication Data

US 2009/0217436 P1 Aug. 27, 2009

(51) Int. Cl.
*A01H 5/00* (2006.01)

(52) U.S. Cl. ..... Plt./209

(58) Field of Classification Search ..... Plt./209
See application file for complete search history.

*Primary Examiner*—June Hwu
(74) *Attorney, Agent, or Firm*—Foley & Lardner LLP

(57) ABSTRACT

This invention relates to a new and distinct variety of strawberry plant named 'VALOR'. This new strawberry plant named 'VALOR' is primarily adapted to the growing conditions of the central coast of California, and is primarily characterized by its medium plant size; medium to large fruit; red to dark red fruit color; strong fruit skin firmness; medium to dark green foliage; good fruit flavor; medium sized foliage and short fruiting trusses.

5 Drawing Sheets

Latin name of the genus and species of the plant claimed: *Fragaria ananassa.*

Variety denomination: 'VALOR'.

BACKGROUND OF THE INVENTION

The present invention relates to a new and distinct strawberry variety named 'VALOR'. This new variety is a result of a controlled cross made in 2001 in an ongoing breeding program between strawberry variety designated 'PS-1269' (patented, U.S. Plant Pat. No. 10,686) and the unpatented strawberry breeding line designated 'PS-3003'. It is unknown as to which strawberry parent is the seed parent and which strawberry parent is the pollen parent. The variety is botanically known as *Fragaria ananassa.*

The seedling resulting from the aforementioned cross was selected from a controlled breeding plot in Ventura County, Calif. in the fall of 2003. After its selection, the new variety was asexually propagated by stolons in a nursery located in San Joaquin County, Calif. The new variety was extensively tested over the next several years in Ventura County, Calif. This propagation has demonstrated that the combination of traits disclosed herein as characterizing the new variety are fixed and remain true to type through successive generations of asexual reproduction.

BRIEF SUMMARY OF THE INVENTION

'VALOR' is primarily adapted to the climate and growing conditions of the central coast of California. The nearby Pacific Ocean provides the needed humidity and moderate temperatures to produce a strong vigorous plant and maintain fruit quality during the fall production months.

The following traits have been repeatedly observed and are determined to be unique characteristics of 'VALOR', which in combination distinguish this strawberry plant as a new and distinct variety:

1. Medium plant size;
2. Medium to large fruit size;
3. Red to dark red fruit color;
4. Strong fruit skin firmness;
5. Medium to dark green foliage color;
6. Good fruit flavor;
7. Medium sized foliage; and
8. Short fruiting trusses.

The new strawberry variety 'VALOR' differs from the parental strawberry varieties 'PS-1269' (patented, U.S. Plant Pat. No. 10,686) and the unpatented strawberry breeding line 'PS-3003', by the following characteristics:

1. Type of bearing: 'VALOR' is everbearing while 'PS-1269' is partial everbearing and 'PS-3003' is everbearing;
2. Firmness of the skin: 'VALOR' is strong while 'PS-1269' is medium and 'PS-3003' is strong;
3. Fruit color: 'VALOR' is red to dark red while 'PS-1269' is red and 'PS-3003' is orange red to red; and
4. Plant vigor: 'VALOR' is medium while 'PS-1269' is medium to large and 'PS-3003' is medium.

The strawberry variety that is believed to be most closely related to the new strawberry variety 'VALOR' is 'PS-2880' (patented, U.S. Plant Pat. No. 15,597). In comparison to the similar strawberry variety 'PS-2880', the new strawberry variety 'VALOR' differs by the following combination of characteristics as described in Table 1:

TABLE 1

| Characteristic | 'VALOR' | 'PS-2880' (U.S. Plant Pat. No. 15,597) |
|---|---|---|
| 1. Average fruit weight (gm) | 23.3 | 20.7 |

TABLE 1-continued

| Characteristic | 'VALOR' | 'PS-2880' (U.S. Plant Pat. No. 15,597) |
|---|---|---|
| 2. Marketable yield (gm/plt) | 566 | 457 |
| 3. Unevenness of fruit surface | Weak | Medium to strong |
| 4. Insertion of achenes | Level with to below the surface | Above the surface |
| 5. Attitude of calyx | Spreading | Spreading to reflexed |
| 6. Firmness of the skin | Strong | Medium |
| 7. Plant size | Medium | Medium to large |
| 8. Average number of stolons | Medium | Few |
| 9. Foliage color (upper surface) | Medium to dark green | Light to medium green |
| 10. Interveinal leaf blistering | Medium | Medium to strong |
| 11. Foliage size | Medium | Medium to large |
| 12. Fruiting truss length (cm) | 20.5 | 27.1 |

For identification a series of AFLP molecular markers have been determined for this new variety.

BRIEF DESCRIPTIONS OF THE PHOTOGRAPHS

The accompanying color photographs illustrate the overall appearance of typical specimens of the new strawberry variety 'VALOR', at various stages of development as true as it is reasonably possible with color reproductions of this type. Color in the photographs may differ slightly from the color value cited in the botanical description which accurately describe the color of 'VALOR'. The depicted plant and plant parts of the new strawberry variety 'VALOR' were taken in Ventura County, Calif., and are approximately 3 to 4 months old.

DETAILED BOTANICAL DESCRIPTION

Figure 1:
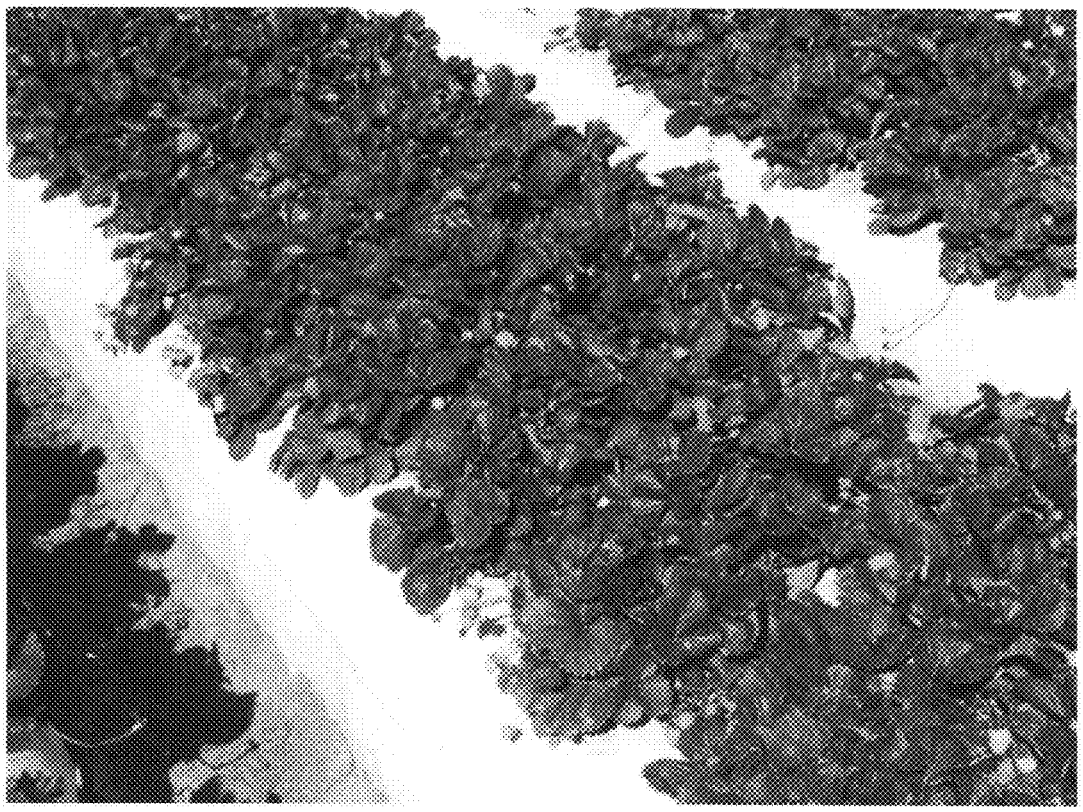
FIG. 1 shows typical fruiting field characteristics of 'VALOR' taken in the month of October 2007.
Figure 2:
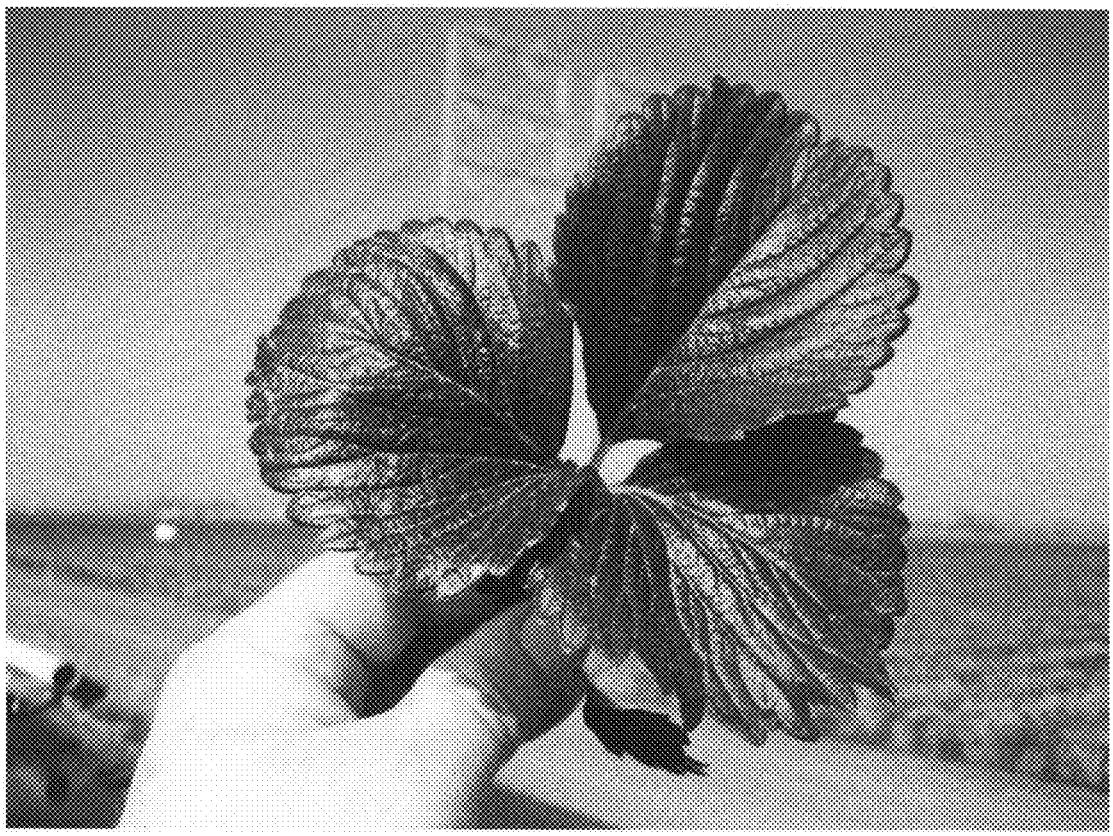
FIG. 2 shows a close-up view of a typical leaf structure of 'VALOR' taken in the month of November 2007.
Figure 3:
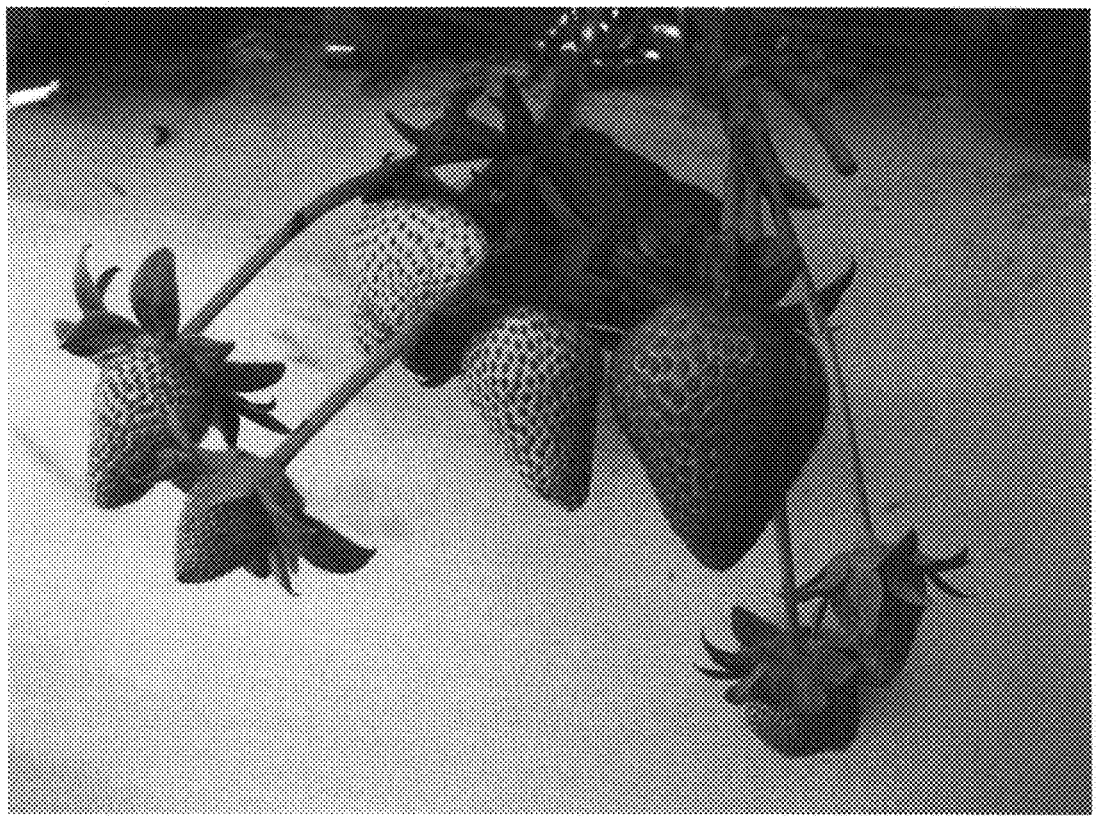
FIG. 3 shows typical mature and immature field fruit of 'VALOR' taken in the month of October 2007.
Figure 4:
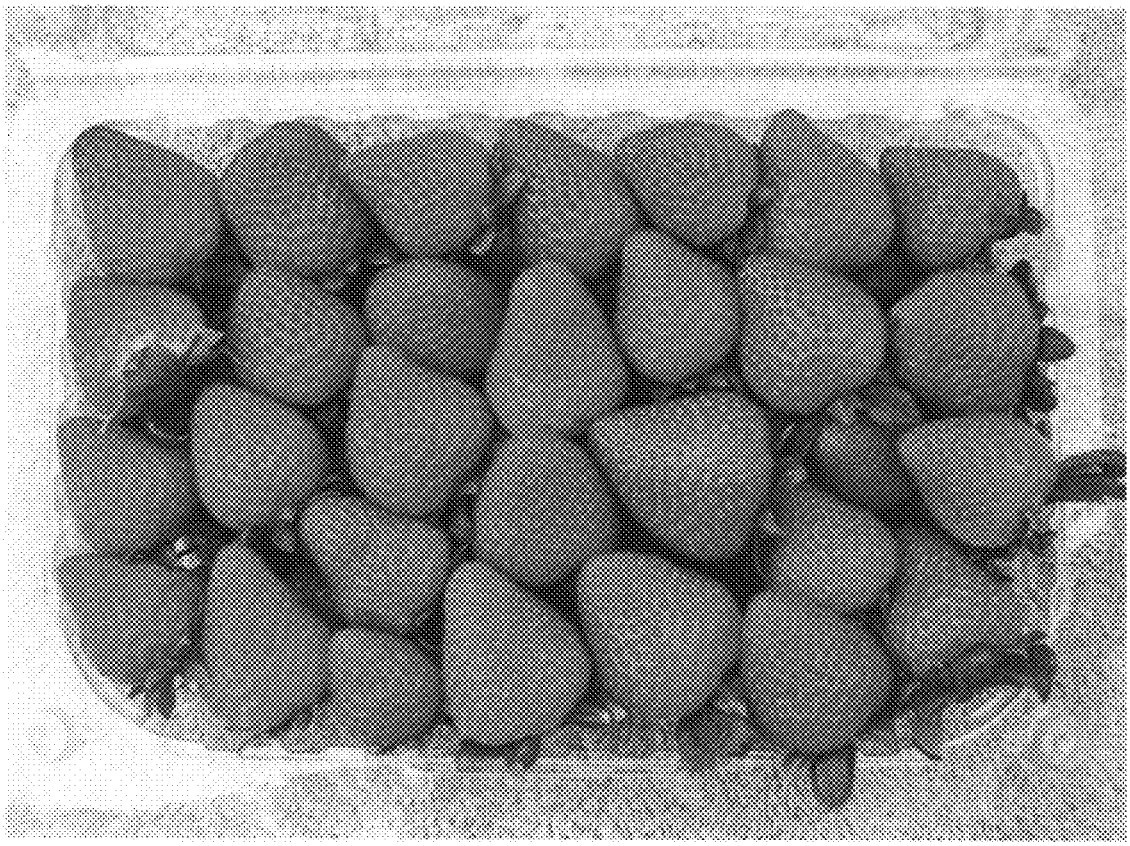
FIG. 4 shows a close-up view of mature fruit of 'VALOR' taken in the month of October 2007.
Figure 5:
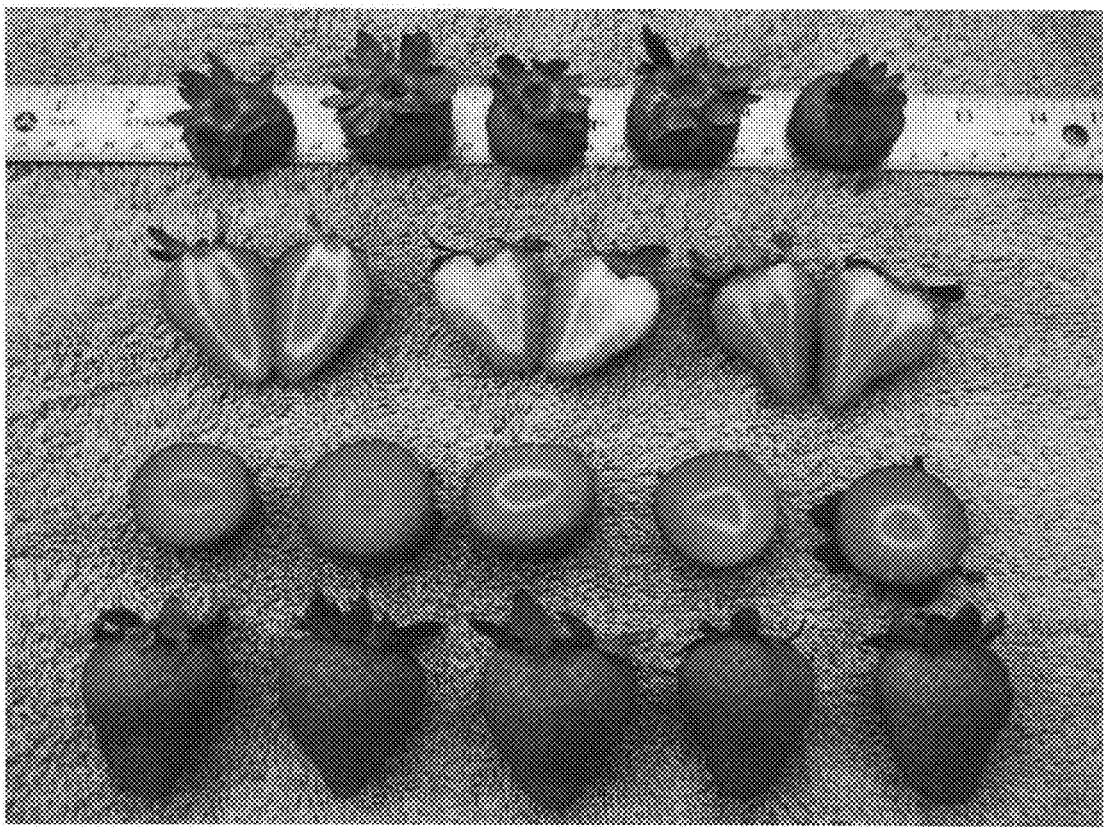
FIG. 5 shows typical internal and external mature fruit characteristics of 'VALOR' taken in the month of October 2007.

'VALOR' has not been observed under all possible environmental conditions. The characteristics of the new variety may vary in detail, depending upon variations in environmental factors, including weather (temperature, humidity and light intensity), day length, soil type and location.

The aforementioned photographs, together with the following description of the new variety 'VALOR', unless otherwise noted, is based on observations taken during the 2007 growing season in Ventura County, Calif. These measurements and ratings were taken from plants of 'VALOR' dug from a low-elevation nursery located in San Joaquin County, Calif., during late January 2007 and planted approximately 6 months later in Ventura County, Calif. The approximate age of the observed plants is 3 to 4 months. Yield observations and fruit quality characteristics are averaged from four years of data collected from the 2004 through 2007 growing seasons. Flower measurements and characteristics are from secondary flowers unless otherwise noted. Fruit characteristics and measurements are from secondary fruit unless otherwise noted.

Color terminology where noted follows the Munsell Book of Colors, Munsell Color, Baltimore, Md. (1976).

The following tables 2–8 describe fruit, plant, stolon, foliage, fruiting truss, flower and pest disease characteristics of the new strawberry 'VALOR' in comparison to the similar strawberry variety 'PS-2880' (patented, U.S Plant Pat. No. 15,597).

TABLE 2

FRUIT CHARACTERISTICS

| Characteristic | 'VALOR' | 'PS-2880' (U.S. Plant Pat. No. 15,597) |
|---|---|---|
| Color of mature fruit | 7.5R 3/8 to 4/10 Red to dark red | 7.5R 4/8 to 3/8 Red |
| Color of internal flesh | 7.5R 3/12 to 4/12 Red to dark red | 7.5R 3/12 to 4/12 Red to dark red |
| Color of fruit core | 7.5R 4/10 to 4/12 Red | 7.5R 4/12 to 5/12 Red |
| Length (cm) | 4.3 | 4.7 |
| Width (cm) | 3.8 | 3.6 |
| Ratio length/ width | 1.13 Slightly longer than broad | 1.29 Slightly longer than broad |
| Calyx diameter (cm) | 4.9 | 5.2 |
| Average weight (gm) | 23.6 | 20.7 |
| Achene color | 5Y 5/6 to 7.5R 3/8 | 5Y 6/8 to 7.5R 3/8 |
| Achenes per berry | 406 | 364 |
| Achene weight (mg) | 0.48 | 0.53 |
| Marketable yield (gm/plt) | 566 | 457 |
| Size | Medium to large | Medium |
| Predominant shape | Conical | Conical to wedged |
| Difference in shapes between primary and secondary fruit | Slight to moderate | Moderate |
| Band without achenes | Absent or very narrow | Absent or very narrow |
| Unevenness of surface | Weak | Medium to strong |
| Evenness of color | Even | Even to slightly uneven |
| Glossiness | Medium to strong | Medium to strong |
| Insertion of achenes | Level with to below the surface | Above the surface |
| Insertion of calyx | In the basin | In the basin to level |
| Attitude of the calyx | Spreading | Spreading to reflexed |
| Size of calyx in relation to fruit diameter | Slightly larger | Slightly larger |
| Adherence of calyx | Strong | Weak |
| Firmness of skin | Strong | Medium |
| Firmness of flesh | Firm | Firm |
| Distribution of red color of the flesh | Marginal and central | Marginal and central |
| Hollow center expression | Absent or very weak | Strong to moderate |
| Flavor | Good | Fair to good |

TABLE 2-continued

| FRUIT CHARACTERISTICS | | |
|---|---|---|
| Characteristic | 'VALOR' | 'PS-2880' (U.S. Plant Pat. No. 15,597) |
| Soluble solids (% brix) | 8.0 | 7.7 |
| Time of first flowering | Early to medium | Early to medium |
| Time of first harvesting | Early to medium | Early to medium |
| Harvest period | Late September to mid December | Late September to mid December |
| Type of bearing | Everbearing | Everbearing |
| Keeping quality | Very good | Good |

TABLE 3

| PLANT CHARACTERISTICS | | |
|---|---|---|
| Characteristic | 'VALOR' | 'PS-2880' (U.S. Plant Pat. No. 15,597) |
| Height (cm) | 22.2 | 26.4 |
| Spread (cm) | 35.1 | 35.8 |
| Size | Medium | Medium to large |
| Habit | Globose | Globose |
| Density | Medium | Medium |
| Vigor | Medium | Medium to strong |

TABLE 4

| STOLON CHARACTERISTICS | | |
|---|---|---|
| Characteristic | 'VALOR' | 'PS-2880'(U.S. Plant Pat. No. 15,597) |
| Average stolon number per plant from the fruiting field | 6.1<br>Medium to few | 5.3<br>Few |
| Anthocyanin coloration | 7.5R 4/8 to 5/8 | 7.5R 4/6 to 5/6 |
| Anthocyanin intensity | Medium to weak | Medium |
| Diameter at bract (mm) | 3.2<br>Medium to thick | 3.3<br>Medium to thick |
| Pubescence | Strong | Strong |

TABLE 5

| FOLIAGE CHARACTERISTICS | | |
|---|---|---|
| Characteristic | 'VALOR' | 'PS-2880' (U.S. Plant Pat. No. 15,597) |
| Foliage: | | |
| Color of upper surface | 7.5GY 2/4 to 3/4<br>Medium to dark green | 7.5GY 3/4 to 4/4<br>Light to medium green |
| Color of under side | 5GY 5/4 to 6/4<br>Light grey green | 5GY 5/4 to 6/4<br>Light grey green |
| Shape in cross section | Slightly concave to flat | Slightly concave to flat |
| Interveinal blistering | Medium | Medium to strong |
| Glossiness | Medium | Medium to strong |
| Number of leaflets | Three | Three |

TABLE 5-continued

| FOLIAGE CHARACTERISTICS | | |
|---|---|---|
| Characteristic | 'VALOR' | 'PS-2880' (U.S. Plant Pat. No. 15,597) |
| Terminal Leaflet: | | |
| Length (cm) | 8.5 | 10.3 |
| Width (cm) | 8.6 | 8.8 |
| Length/width ratio | 0.98 | 1.18 |
| Serrations/ leaf | 20.3 | 22.9 |
| Size | Medium | Medium to large |
| Shape of base | Obtuse | Acute |
| Shape of teeth | Obtuse | Obtuse |
| Petiole: | | |
| Length (cm) | 14.8 | 13.9 |
| Diameter (mm) | 4.1 | 4.3 |
| Color of petiole | 5GY 5/6 to 6/6<br>Yellow green | 5GY 7/6 to 7/8<br>Yellow green |
| Petiolule length (mm) | 14.3 | 15.3 |
| Color of petiolule | 5GY 5/6 to 6/6<br>Yellow green | 5GY 7/6 to 7/8<br>Yellow green |
| Pubescence | Sparse | Moderate |
| Attitude of hairs | Slightly outward | Slightly outward |
| Stipule: | | |
| Length (mm) | 24.9 | 26.3 |
| Width (mm) | 11.6 | 9.2 |
| Anthocyanin coloration | Weak<br>10RP 4/10 to 4/12<br>Red purple | Weak<br>7.5RP 5/10 to 5/12<br>Red purple |
| Color of stipule | 2.5GY 4/4 to 4/6<br>Medium green | 2.5GY 4/6 to 5/6<br>Medium to light green |

TABLE 6

| FRUITING TRUSS CHARACTERISTICS | | |
|---|---|---|
| Characteristic | 'VALOR' | 'PS-2880' (U.S. Plant Pat. No. 15,597) |
| Length (cm) | 20.5 | 27.1 |
| Position relative to foliage | Level with | Level with |
| Pubescence | Medium to strong | Medium |
| Anthocyanin intensity | Very light to none<br>5R 4/8 to 5/8<br>Greyed red | Light<br>2.5R 5/6 to 6/6<br>Greyed red |
| Attitude at first pick | Prostrate | Prostrate |

TABLE 7

| FLOWER CHARACTERISTICS | | |
|---|---|---|
| Characteristic | 'VALOR' | 'PS-2880' (U.S. Plant Pat. No. 15,597) |
| Petal color | N 9.5/90.0% R to 9.25/84.2% R<br>White | N 9.5/90.0% R to 9.25/84.2% R<br>White |
| Sepal color | 7.5GY 4/4 to 3/4<br>Green | 7.5GY 4/4 to 3/4<br>Green |
| Corolla diameter (mm) | 32.5<br>Medium to large | 33.6<br>Medium to large |
| Calyx diameter (mm) | 40.9 | 34.1 |
| Petal length (mm) | 12.5 | 13.0 |

TABLE 7-continued

FLOWER CHARACTERISTICS

| Characteristic | 'VALOR' | 'PS-2880' (U.S. Plant Pat. No. 15,597) |
|---|---|---|
| Petal width (mm) | 12.7 | 13.8 |
| Petal length/width ratio | 0.99 | 0.95 |
| Petals/flower | 5.7 | 6.5 |
| Sepal length (mm) | 15.6 | 12.3 |
| Sepal width (mm) | 6.9 | 4.4 |
| Sepal length/width ratio | 2.25 | 2.78 |
| Sepals/flower | 11.7 | 12.3 |
| Size of calyx relative to corolla | Larger | Same size to larger |
| Size of inner calyx relative to outer calyx | Smaller | Smaller |
| Relative position of petals | Touching to overlapping | Overlapping |

TABLE 8

PEST AND DISEASE REACTIONS

| Characteristic | 'VALOR' | 'PS-2880' (U.S. Plant Pat. No. 15,597) |
|---|---|---|
| Two spotted spider mite | Moderately susceptible | Moderately susceptible |
| Lygus bug | Susceptible | Susceptible |
| Flower thrips | Moderately susceptible | Moderately susceptible |
| Powdery mildew | Susceptible | Susceptible |
| Botrytis fruit rot | Moderately susceptible | Moderately susceptible |
| Angular leaf spot | Moderately susceptible | Susceptible |

We claim:

1. A new and distinct strawberry plant named 'VALOR', as herein described and illustrated by the characteristics set forth above.

* * * * *